United States Patent [19]
Schneider et al.

[11] Patent Number: 4,648,400
[45] Date of Patent: Mar. 10, 1987

[54] OPHTHALMIC SURGERY SYSTEM

[75] Inventors: Richard T. Schneider, Gainesville, Fla.; Richard H. Keates, Columbus, Ohio

[73] Assignee: RTS Laboratories, Inc., Gainesville, Fla.

[21] Appl. No.: 731,121

[22] Filed: May 6, 1985

[51] Int. Cl.$^4$ .............................................. A61B 17/36
[52] U.S. Cl. .................................... 128/303.1; 128/395; 219/121 LA; 219/121 LQ; 219/121 LR; 219/121 LZ
[58] Field of Search ...................... 128/303.1, 395–398; 219/121 LA, 121 LB, 121 LP, 121 LQ, 121 LR, 121 LZ

[56] References Cited

U.S. PATENT DOCUMENTS

| | | | |
|---|---|---|---|
| Re. 22,534 | 8/1944 | Prouty | 128/397 |
| 1,965,947 | 7/1934 | Prouty | 128/397 |
| 2,930,379 | 3/1960 | Dopp et al. | 128/396 |
| 3,315,680 | 4/1967 | Silbertrust et al. | 128/395 |
| 3,348,547 | 10/1967 | Kavanagh | 128/395 |
| 3,417,754 | 12/1968 | Smart | 128/395 |
| 3,456,651 | 7/1969 | Smart | 128/395 |
| 3,467,099 | 9/1969 | Lotmar | 128/395 |
| 3,481,340 | 12/1969 | McKnight et al. | 128/395 |
| 3,487,835 | 1/1970 | Koester et al. | 128/395 |
| 3,528,424 | 9/1970 | Ayres | 128/303.1 |
| 3,566,872 | 3/1971 | Draeger et al. | 128/303.1 |
| 3,621,198 | 11/1971 | Herbrich | 128/397 |
| 3,642,007 | 2/1972 | Roberts et al. | 128/395 |
| 3,670,260 | 6/1972 | Koester et al. | 128/395 |
| 3,703,176 | 11/1972 | Vassiliadis et al. | 128/395 |
| 3,710,798 | 1/1973 | Bredemeier | 128/303.1 |
| 3,712,984 | 1/1973 | Lienhard | 250/504 |
| 3,720,213 | 3/1973 | Hobart et al. | 128/395 |
| 3,750,670 | 8/1973 | Palanos et al. | 128/395 |
| 3,806,829 | 4/1974 | Duston et al. | 219/121 LB |
| 3,865,113 | 2/1975 | Sharon et al. | 128/303.1 |
| 3,910,276 | 10/1975 | Polanyi et al. | 128/303 |
| 3,913,582 | 10/1975 | Sharon | 128/303.1 |
| 3,914,013 | 10/1975 | Rosenberg | 128/303.1 |
| 3,943,931 | 3/1976 | Krasnov | 128/303.1 |
| 3,982,541 | 9/1976 | L'Esperance, Jr. | 128/303.1 |
| 4,069,823 | 1/1978 | Isakov et al. | 128/303.1 |
| 4,122,853 | 10/1978 | Smith | 128/303.1 |
| 4,165,744 | 8/1979 | Cravy et al. | 128/303.1 |
| 4,270,845 | 6/1981 | Takizawa et al. | 128/303.1 |
| 4,309,998 | 1/1982 | Aron et al. | 128/303.1 |
| 4,313,093 | 1/1982 | Suenaga et al. | 128/303.1 |
| 4,359,308 | 11/1982 | Nakajima et al. | 128/303.1 |
| 4,381,007 | 4/1983 | Doss | 128/303.1 |
| 4,391,275 | 7/1983 | Fankhauser et al. | 128/303.1 |
| 4,397,310 | 8/1983 | Pomerantzeff | 128/303.1 |
| 4,408,602 | 10/1983 | Nakajima | 128/303.1 |
| 4,409,979 | 10/1983 | Roussel et al. | 128/303.1 |
| 4,461,294 | 7/1984 | Baron | 128/303.1 |

FOREIGN PATENT DOCUMENTS

| | | | |
|---|---|---|---|
| 0111060 | 6/1984 | European Pat. Off. | 128/303.1 |
| 2108282 | 5/1983 | United Kingdom | 128/303.1 |

OTHER PUBLICATIONS

Srinivasan et al., "Excimer Laser . . . Cornea", Am. J. Opth., 96:710–715, 1983.
Tabaoda et al., "Response . . . Laser Pulses", Health Physics, vol. 40, May 1981, pp. 677–683.

Primary Examiner—Lee S. Cohen
Attorney, Agent, or Firm—Merchant, Gould, Smith, Edell, Welter and Schmidt

[57] ABSTRACT

An ophthalmic surgery system (10) for performing corneal keratotomies and resectomies utilizes a light source (12) which generates a pulsed beam in the ultraviolet/vacuum ultraviolet region. The beam is received by a sealed base unit (16) and attached rotatable subunit (18) which shape, focus, and project the beam onto a protective mask (20) mounted directly on the eye (22) of a patient. The mask (20) includes a normally closed shutter (148) which opens responsive to a counter (32) positioned along the beam path and sensors (156) positioned on opposite sides of a control slit (154) to apply a predetermined number of pulses while the mask is aligned to effect precise cutting of the cornea to the desired depth.

27 Claims, 13 Drawing Figures

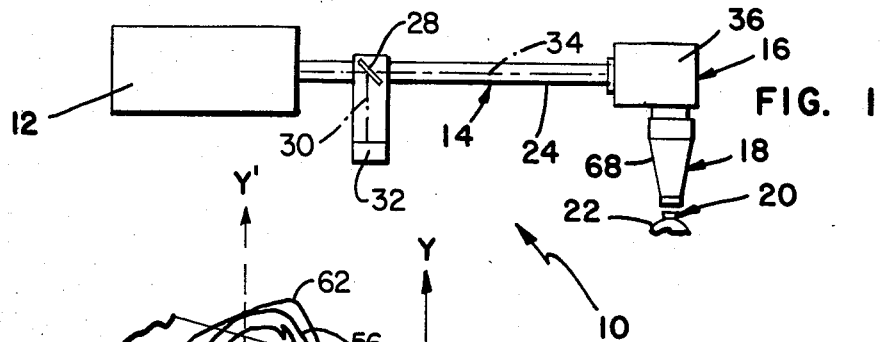
FIG. 1
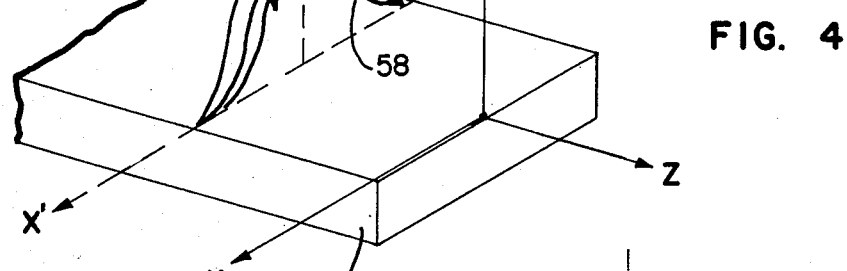
FIG. 4
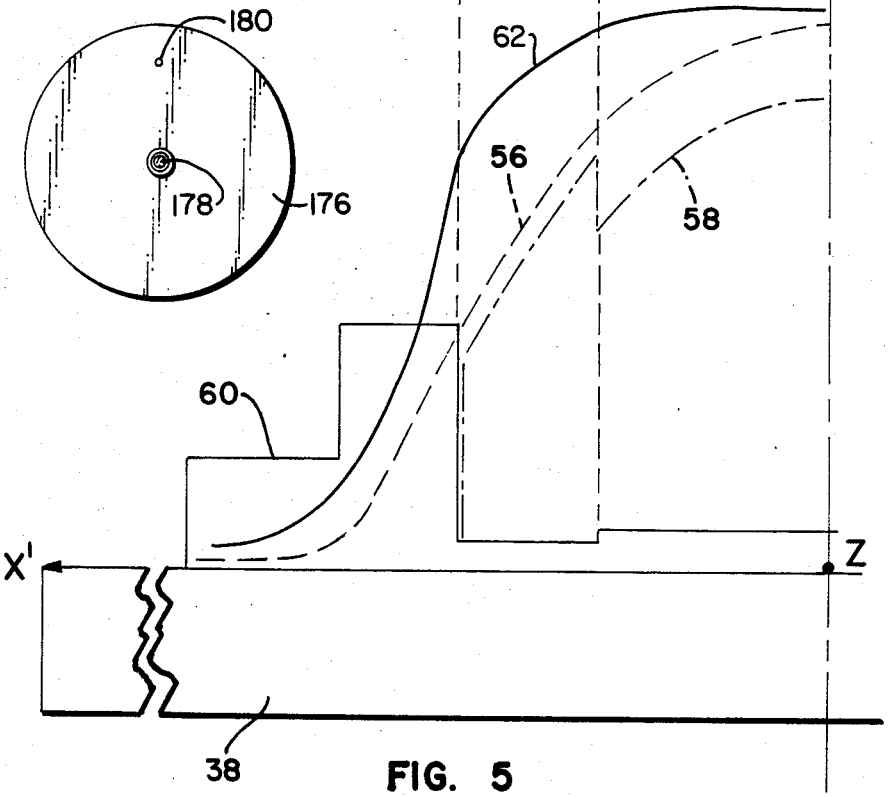
FIG. 12
FIG. 5

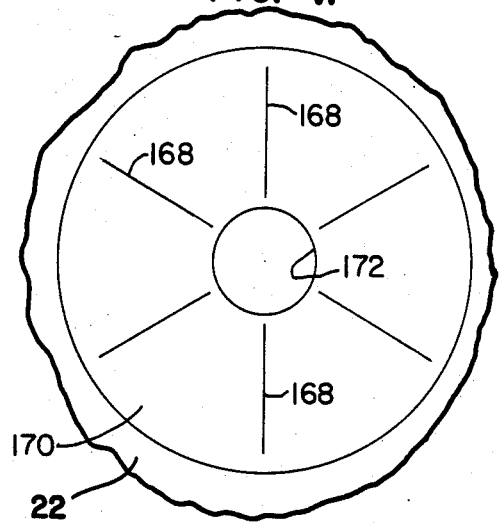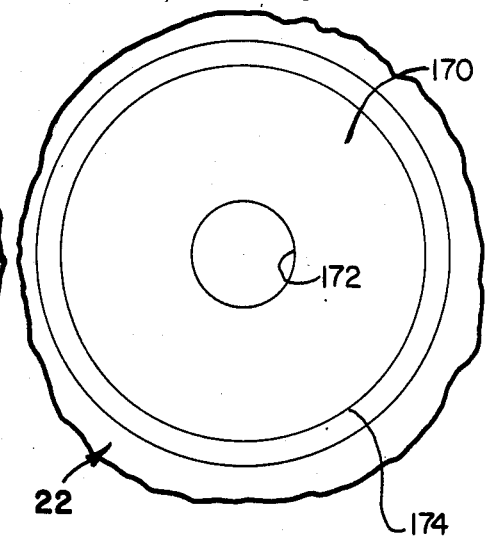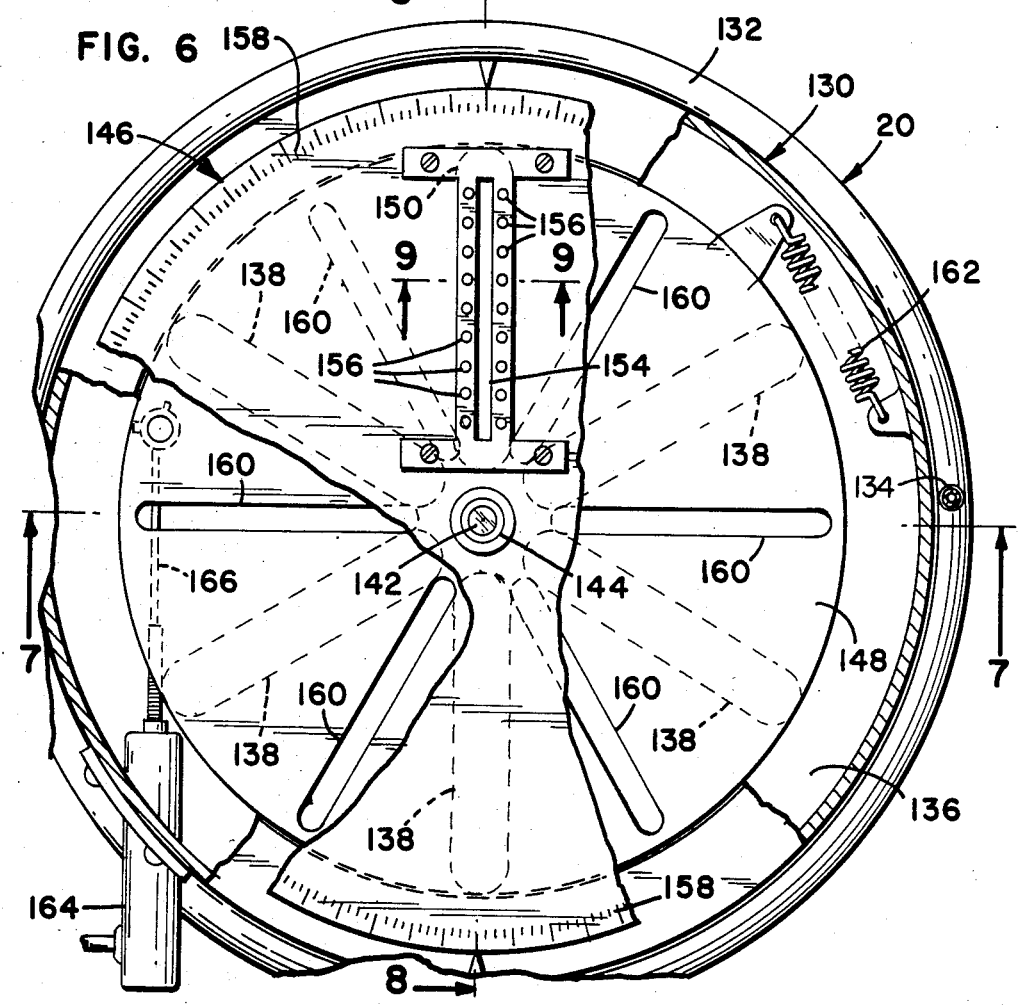

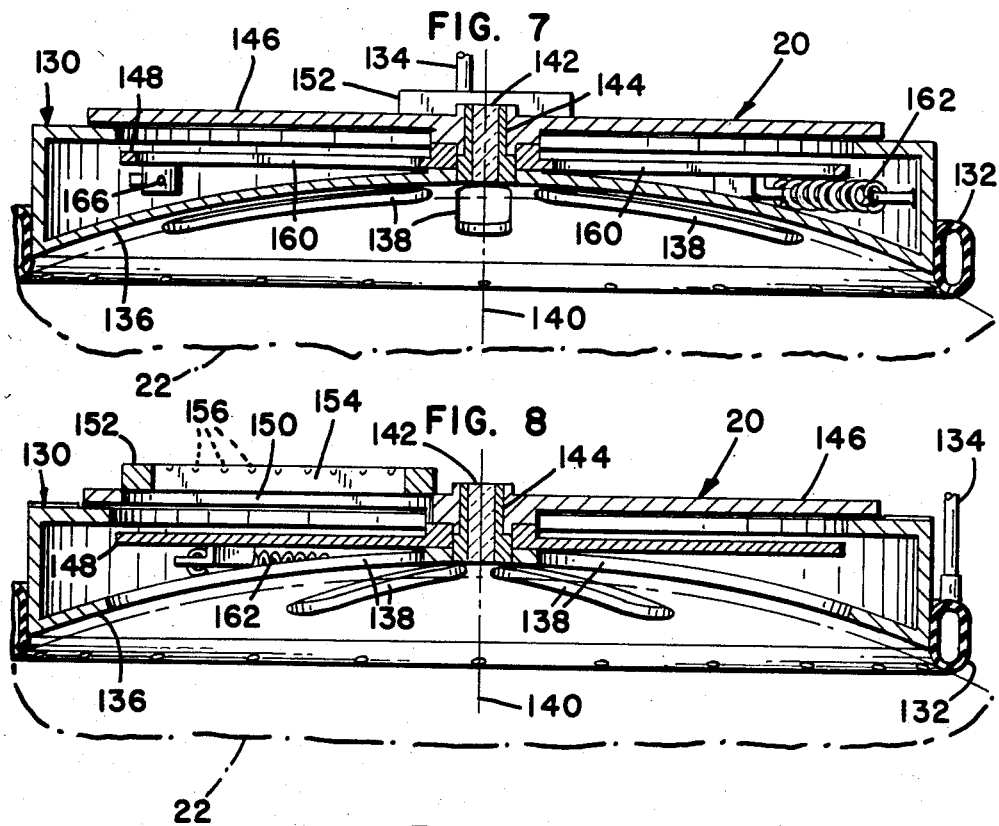
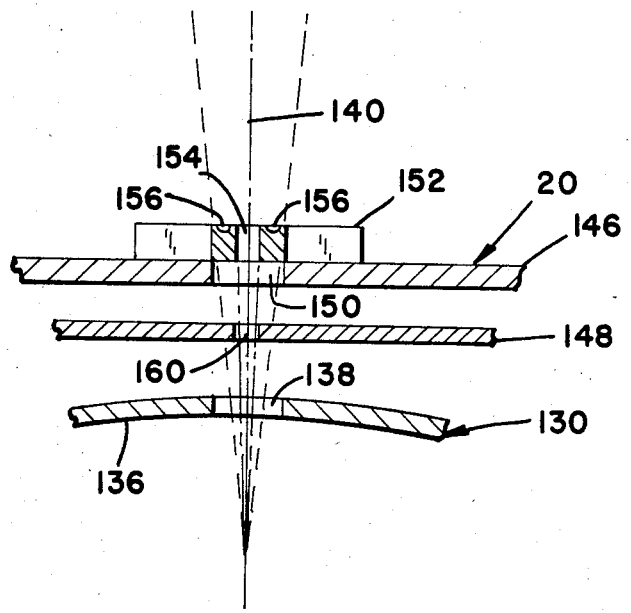

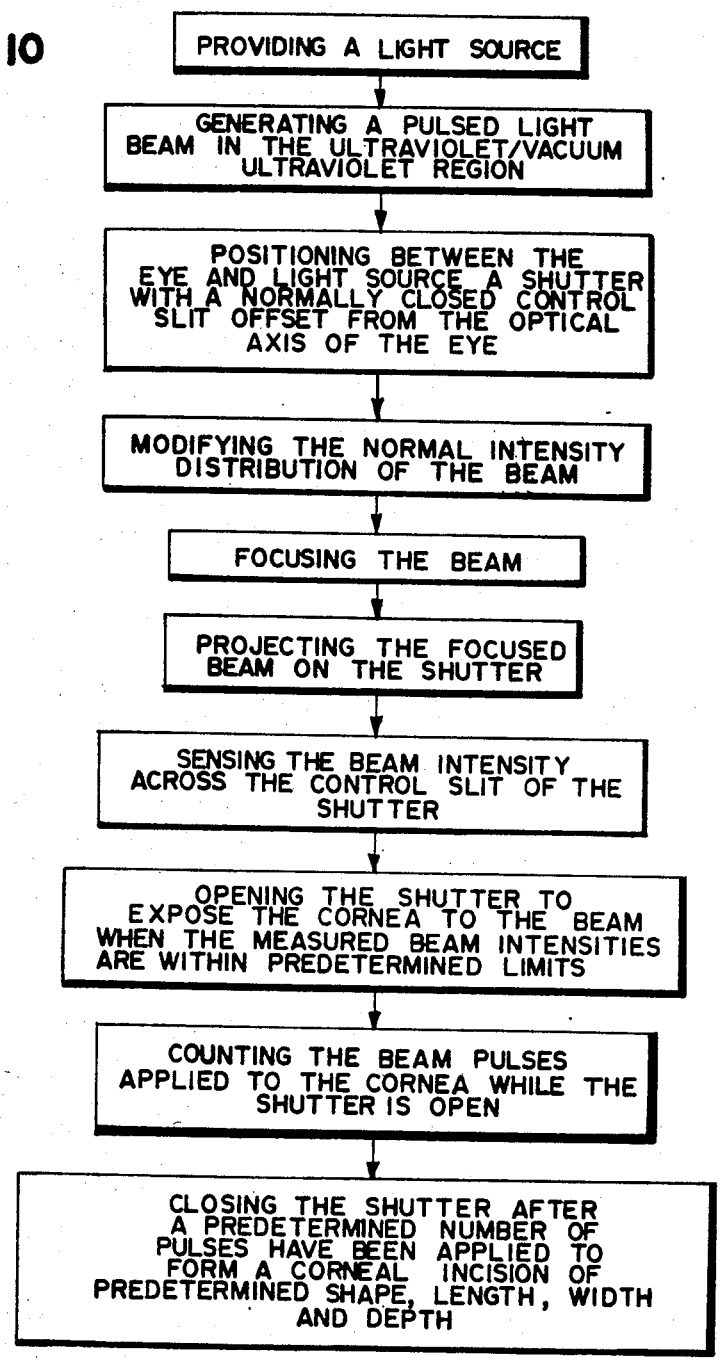

OPHTHALMIC SURGERY SYSTEM

TECHNICAL FIELD

The present invention relates generally to an ophthalmic surgery system. More particularly, this invention concerns a system incorporating a high-energy light source in the ultraviolet/vacuum ultraviolet region for performing keratotomies and resectomies.

BACKGROUND ART

A major percentage of the American population is myopic or nearsighted. Glasses and contact lenses have been the two most common approaches to correction of nearsightedness. Another approach is the radial keratotomy, whereby a number of precise incisions are made directly into the cornea of the eye in radial fashion about the central uncut optical zone of the cornea to relax its radius of curvature thereby increasing the focal length to correct or improve vision.

It will be appreciated, however, that radial keratotomies are extremely delicate procedures requiring extreme precision and safety. Eyes in general, and corneas in particular, are extremely sensitive and delicate. The cornea is a transparent lens tissue covering the iris and pupil through which light is admitted into the eye. The sizes and thicknesses of corneas vary from patient to patient. In performing a radial keratotomy, the length, width, depth and spacing of the incisions must be precisely controlled in order to accomplish the desired result without otherwise damaging the eye or cornea. This is complicated by the fact that eyes are subject to involuntary movements and are difficult to stabilize.

The history of radial keratotomy dates back to about 1869 when Snellen first described surgical methods for the correction of astigmatisms and raised the possibility of altering corneal curvature to correct vision. However, it was not until 1894 when Bates attempted to do just that by using a method called unsutured wedge resection. This essentially involved removing wedge-shaped sections of the cornea along radial lines centered on the visual axis.

In 1939, Sato reported on a series of cases in which incisions were performed on both the anterior (inside) and posterior (outside) surfaces of the cornea. The purpose of these incisions was to correct the preexisting irregular astigmatisms. His work in this field culminated in a paper presented in 1953 in which, once again, radiating incisions in both the anterior and posterior surfaces of the cornea were performed. Sato's incisions were intended to reduce a preexisting spherical myopia, i.e., no astigmatism. This procedure was successful with some of Sato's patients, however, unfortunately about 60–70% developed corneal edema or "fogging" of the corneal tissue.

Following Sato's work, others attempted to duplicate and improve on his basic concept. These individuals included the likes of Belyaev, Kio Tin and Yenaliev, among others. These procedures were relatively crude. Surgical loupes similar to jeweler's loupes were used for magnification. The incisions were performed with hand-honed, handheld unguarded surgical knives. The size of the optical zone, and the length and depth of the incisions, were estimated by eye.

It wasn't until the early 1970's that there were any significant breakthroughs in both the conceptual approach and surgical techniques for radial keratotomies. Fyodorov and Durnev demonstrated that permanent changes in corneal curvature could be induced by using partially penetrating radial incisions on only the anterior surface of the cornea. Fyodorov utilized high-powered stereoscopic operating microscopes to improve illumination and the amount and quality of magnification. High-carbon steel razor fragments were used for extremely clean incisions, and a micrometer adjustable blade holder with an attached quard were utilized to control the depth of the incision. Fyodorov also developed a device which, when pressed against the corneal surface, would leave a temporary circular mark to delineate the boundary of the optical zone. Corneal pachometers have since been developed for accurately measuring the thickness of corneas and, with the aid of computers, this information can in turn be used to map corneal topologies. However, despite these advances, radial keratotomies still tend to be regarded as experimental and unpredictable.

In contrast to mechanical cutting of tissue by surgical knives, high-intensity light sources such as lasers have heretofore been adapted to some forms of eye surgery, but have not been suitable for use in radial keratotomies for various reasons. Earlier applications of laser eye surgery involved mostly internal cauterizing and photocoagulation, instead of cutting. Photocoagulation devices are intended for treatment of the retina, and must therefore use radiation which penetrates the cornea, lens, and both humors without significant absorption and thus damage to these organs. Radial keratotomies require precision positioning of the beam and maximum absorption over a precise depth without penetrating the cornea tissue. Hand-held laser scalpels are completely impractical for such surgery.

Heretofore there has not been available a device incorporating a light source generating a beam of proper characteristics which could be steered and applied with sufficient precision and safety for radial keratotomy procedures. There is thus a need for an improved ophthalmic surgery system by which corneal keratotomies and resectomies can be performed with the precision, safety and reliability necessary in such procedures.

SUMMARY OF INVENTION

The present invention comprises an ophthalmic surgery system which overcomes the foregoing and other difficulties associated with the prior art. In accordance with the invention, there is provided an apparatus and method which are particularly adapted for performing corneal keratotomies and resectomies.

The system utilizes a pulsed high-intensity light source, which may be coherent or incoherent, generating an invisible cutting beam in the ultraviolet/vacuum ultraviolet region within predetermined wavelength and intensity ranges. The beam is directed to a base unit having a mirror which is treated to shape or attenuate the high-intensity regions for more uniform distribution across the beam as it is reflected through a rotatable subunit attached to the base unit. The base and subunits are preferably under vacuum or filled with suitable gas other than air, so as to minimize beam dissipation and refraction. A beam splitter and counter are provided along the beam path for counting the number of beam pulses. The shaped beam is then focused by a lens and reflected by adjustable mirrors in the subunit through a prism for projection onto a mask covering the patient's eye. The mask is mounted directly on the eye, preferably by means of suction, but it is not mechanically secured to the subunit. The mask includes an alignment window opaque to the cutting beam but transparent to visible light, centered on the patient's optical axis, and a radial slot which is normally closed by a shutter. Arrays of sensors are provided along opposite sides of the slot for controlling a solenoid which opens the shutter to effect optical connection between the beam and the cornea. Application of the cutting beam to the cornea and thus cutting can proceed only when the patient's eye is properly aligned and the intensities along and across the slot are within predetermined ranges. The shutter closes after a predetermined number of beam pulses have been applied to form an incision of the desired length, width, and depth.

DESCRIPTION OF DRAWINGS

A better understanding of the invention can be had by reference to the following Detailed Description in conjunction with the accompanying Drawings, wherein:

FIG. 1 is a schematic view of the ophthalmic surgery system incorporating the invention;

FIG. 4 is a composite perspective diagram of the beam before and after shaping by the treated mirror in the base unit;

FIG. 5 is a composite diagram of the energy intensity across the beam after shaping by the treated mirror in the base unit;

FIG. 6 is an enlarged top view (partially cutaway) of the mask covering the patient's eye;

FIGS. 7, 8 and 9 are sectional views taken along lines 7—7, 8—8 and 9—9, respectively, of FIG. 6 in the direction of the arrows showing further details of the mask.

FIG. 10 is a flowchart of the steps involved in performing a keratotomy in accordance with the invention;

FIG. 11 is a fragmentary illustration of an eye after a keratotomy;

FIG. 12 is a reduced view of a substitute part used in the mask when performing a resectomy; and FIG. 13 is a fragmentary illustration of an eye after a resectomy.

DETAILED DESCRIPTION

Figure 2:
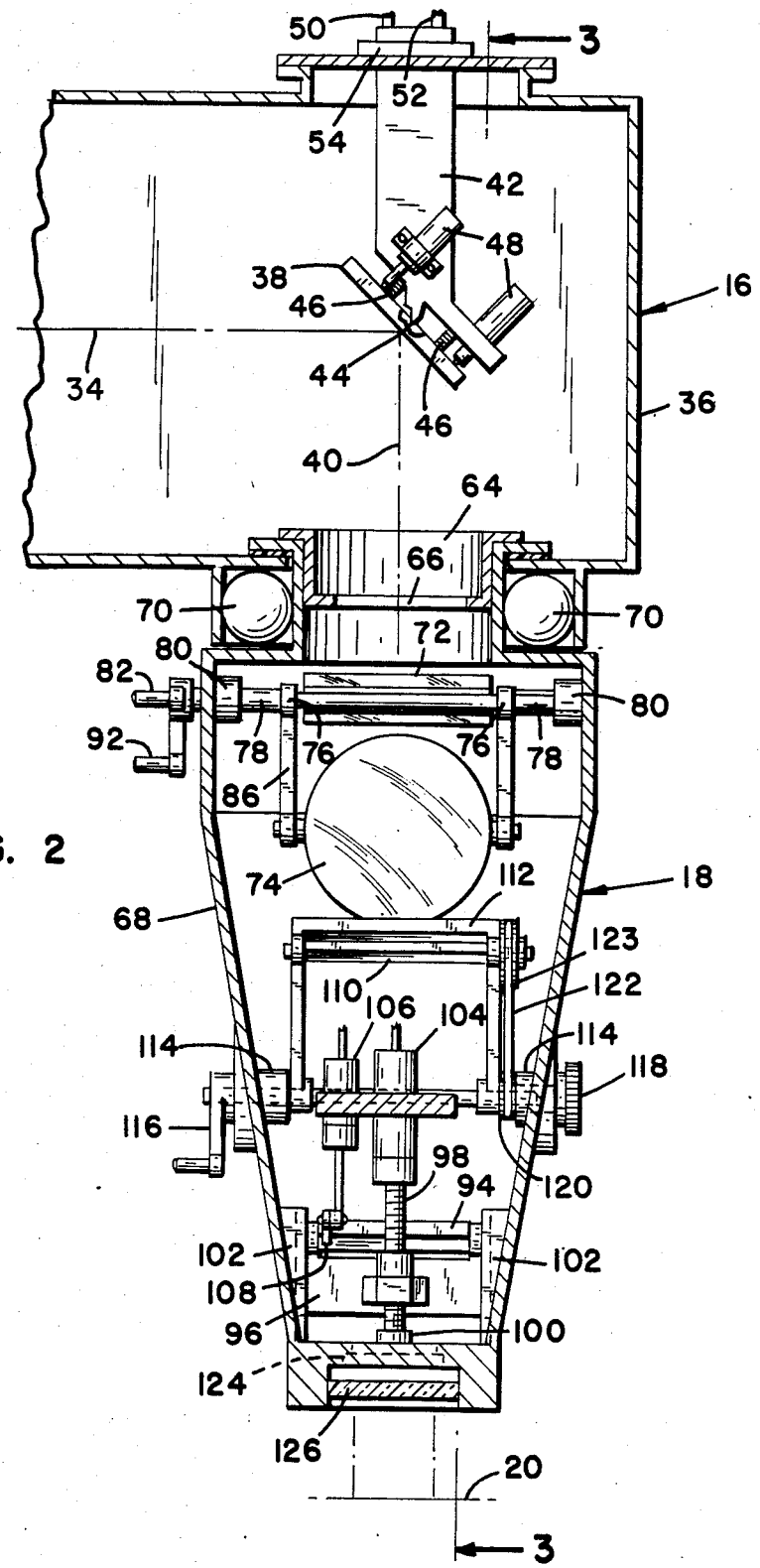
FIG. 2 is an enlarged cutaway diagram of a portion of the base unit and the subunit of the system.

Referring now to the Drawings, wherein like reference numerals designate like or corresponding elements throughout the views, and particularly referring to FIG. 1, there is shown the ophthalmic surgery system 10 of the invention. The system 10 comprises a light source 12 generating a beam that is directed by a beam transporting device 14 to a base unit 16 and then through a subunit 18 for projection onto mask 20 mounted directly on the eye 22 of a patient in order to perform a radial keratotomy. Although the system 10 is particularly adapted for performing keratotomies, it can also be adapted for performing resectomies. As will be explained more fully hereinafter, the system 10 utilizes a light source 12 that generates a beam of predetermined characteristics which is precisely shaped, directed, and applied through the mask 20 to the cornea of eye 22 so that keratotomies and resectomies can be performed with greater control, predictability and safety.

The light source 12 comprises an important component of the system 10, although the particular type of light source is not as critical as the beam radiation it generates. In accordance with the preferred embodiment, the light source 12 comprises a high-intensity light source generating a beam in the ultraviolet (UV) or vacuum ultraviolet (VUV) region which is absorbed in the tissue of the cornea within less than about ten micrometers. For example, such a suitable light source would be one generating a beam of electromagnetic radiation with a wavelength of less than about 2500 Angstroms, preferably between about 1000 and 2000 Angstroms, and an intensity of between about 1 and 10 megawatts per square centimeter. The light source 12 can be of the pulsed or continuous type. For example, an ArF or KrF excimer laser would be a suitable light source 12, although the light souce does not have to be coherent. The radiation generated by the light source 12 is not visible to the naked eye and may be coherent or incoherent, but the tissue-cutting action is the same as will be explained below.

Cutting of tissue can be accomplished by several different mechanisms, including melting or burning and destruction by shock wave. The present invention, however, by utilizing a light source 12 of the above characteristics, accomplishes cutting by breaking or severing the chemical bonds of the organic molecules of the tissue. All living tissue comprises complicated organic molecules that are thermodynamically unstable, which means that the entropy of the molecule is lower than a stable compound of the particular chemical elements involved. Therefore, entropy has to be lowered constantly to prevent these organic molecules from disintegrating. Entropy can only be lowered if energy is added. Consequently, if such organic molecules are no longer supplied with this energy, they will decay into simpler molecules.

The same effect can be obtained if these organic molecules are subjected to a light field (photon field) having a frequency which corresponds to the vibrational frequencies of the molecules. Resonance occurs putting the molecules in a state of high excitation. This additional instability requires further entropy removal, which cannot be met by natural metabolism. Therefore, an accelerated decay process takes place in which the organic molecules separate along their hydrogen/carbon bonds and disintegrate into simpler stable molecules in the gas or vapor phase which can then be aspirated away.

In the present invention, as will be explained more fully hereinafter, the precise number of light pulses required to cut to a predetermined depth are applied, based upon the tissue type (corneal) and the corneal topology of the particular patient. The number of pulses required is predetermined empirically, for the type tissue and light beam, and a counter is used to insure that the precise number of pulses are applied. Pulse counting is preferred because it is relatively less difficult and more accurate than measuring beam intensity. This comprises a significant feature of the present invention.

In contrast to the prior art, the present invention accomplishes separation of the hydrogen/carbon bonds by a single photon instead of an accumulation (pileup) of photons which would otherwise result in destruction of the tissue by heat or shock wave. The present invention utilizes electromagnetic radiation in the wavelength range of about 1000–2500 Angstroms, which is usually referred to as ultraviolet and vacumm ultraviolet radiation. Radiation of less than 3 electron volts will not break chemical bonds using only one photon, and all cutting of tissue so far done in the prior art is by such radiation despite the resultant heating complications.

It should be noted that there is a threshold effect which occurs even for ultraviolet radiation. Above a certain irradiance intensity, a plasma forms just above the tissue surface which will absorb the incident radiation producing an ionized gas that emits secondary radiation and highly excited ions. The formation of plasma in this instance is an undesirable effect which can be mitigated by maintaining the incident radiation below the plasma formation irradiance intensity threshold.

Referring still to FIG. 1, the light beam generated by source 12 is conveyed by the transporting device 14 to the base unit 16. System 10 is illustrated as including a beam transporting device 14 because the light source 12 would typically be located remotely from the base unit 16. For example, a single light source 12 could be used to power multiple systems 10. However, as illustrated, the beam transport device 14 comprises a sealed housing 24 which is preferably evacuated or filled with suitable gas, such as helium, to minimize dissipation and refraction of the beam. The beam transporting device 14 can be constructed in any suitable manner, and its particular construction details are not critical to practice of the invention. Any suitable construction can be utilized. For example, U.S. Pat. Nos. 3,913,582 to Sharon, 3,528,424 to Ayres, 4,393,093 to Suenaga, 4,270,845 to Takizawa, 4,069,823 to Isakov, 4,409,979 to Roussel, and 3,481,340 to McKnight teach various forms of articulated arms for transmitting light beams which could be used in place of beam transporting device 14.

In accordance with the preferred embodiment, a beam splitter 26 is provided in the transport device 14 along the path of the beam between source 12 and the base unit 16. Beam splitter 26 is of substantially conventional construction, including a mirror 28 for reflecting part of the beam along path 30 to a sensor, which in this case comprises a photo diode counter 32 for sensing the number of waves or pulses of energy applied, as will be explained more fully hereinafter. If desired, an energy meter (not shown) can be used with counter 32 to assure that the average energy of pulses applied are within predetermined limits. The remainder of the beam generated by source 12 continues along path 34 to the base unit 16.

Figure 3:
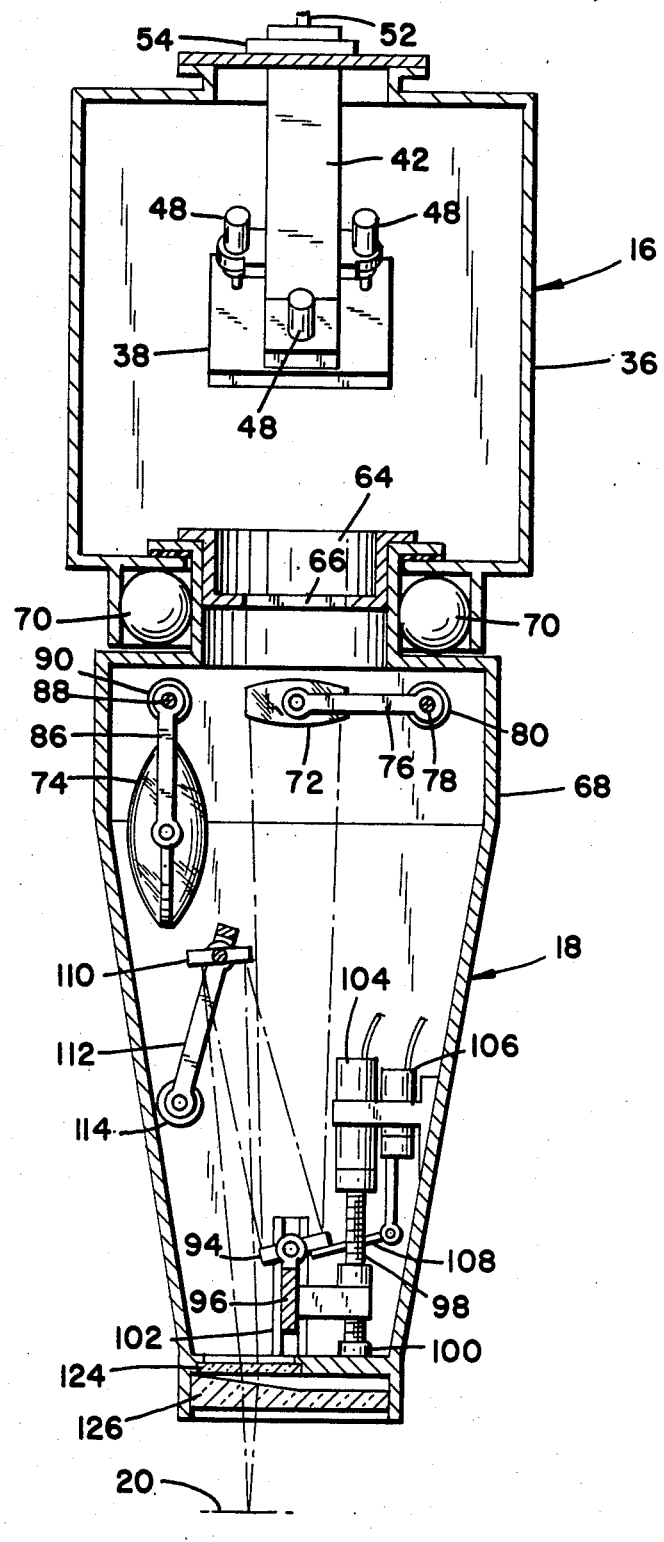
FIG. 3 is a sectional view taken along lines 3—3 of FIG. 2 in the direction of the arrows.

Referring now to FIGS. 2 and 3, the beam from the light source 12 is received by the base unit 16 for reflection and shaping or attenuation. The base unit 16 includes a sealed housing 36 in fluid-tight communication with the housing 24 of the beam transport device 14. The interior of the housing 36 is thus also evacuated or filled with gas such as helium. A flat mirror 38 is mounted within the casing 36 of the base unit 16 for reflecting the beam from path 34 downwardly along path 40 into the subunit 18. Mirror 38 can be fixed or adjustable.

In accordance with the preferred embodiment, the mirror 38 is pivoted to the bottom end of a rotatable holder or post 42. Post 42 includes a stabilization pivot 44 seated in a recess on the rear surface of mirror 38, which is secured to the post by means of multiple springs 46. Three motorized micrometer drives 48 arranged in triangular fashion are also secured between post 42 and mirror 38 for adjustability. Three springs 46 are used, one spring adjacent each drive 48. If desired, the interiors of mirror 38 and post 42 can be bored to define a flow path for circulating coolant therethrough via conduits 50 and 52 extending through a rotatable vacuum seal fitting 54.

Referring now to FIGS. 4 and 5, the face of mirror 38 is preferably treated so as to provide for a more uniform distribution of the energy intensity within the light beam. This is important because, as will be explained more fully hereinafter, the beam must be spread out to fill the mask 20 on the patient's eye.

FIGS. 4 and 5 represent the intensity distributions across the light beam before and after the desired shaping by the surface of mirror 38. Interference filters can be utilized, however, an absorption filter or grey filter is preferred because such only modifies the intensity of the beam regardless of its direction. In accordance with the preferred embodiment, the face of mirror 38 is covered with a partially-absorbing film of variable density across its width and along its length, which may be vacuum-deposited silver, gold, aluminum, or any other suitable material. X represents the long axis of a rectangular beam, and Y represents the short axis. Y' represents an axis for the intensity level along axis Z on the face of mirror 38. Curve 56 in FIGS. 4 and 5 represents the Gaussian intensity profile across the incoming beam. Curve 62 represents the ideal beam intensity profile of the outgoing beam travelling along path 40 after reflection and attenuation by mirror 38. Curve 60 represents the depth of the absorption coating across the face of mirror 38 which results in the actual beam intensity profile 58 of the beam travelling into the subunit 18. This comprises an important feature of the invention.

An optional insert 64 as seen in FIG. 2 can be provided between the base unit 16 and the subunit 18 for externally shaping the beam travelling along path 40, if necessary. The insert 64 fits into a circular opening in the bottom of housing 36, but defines a rectangular opening 66. The insert 64 is used if the light source 12 generates a circular beam. If the light source 12 generates a rectangular beam, the insert 64 is not necessary.

Referring again to FIGS. 2 and 3, the subunit 18 is secured to the underside of base unit 16 for rotation about a vertical axis. In particular, the subunit 18 comprises a sealed housing 68 which is open only to the interior of the base unit 16 so that both units are either under vacuum or filled with suitable gas such as helium. Ball bearings 70 are provided between the units 16 and 18.

The subunit 18 includes optical elements for focusing the beam received along path 40 into a rectangular beam on the mask 20. A lens, which can be either fixed or movable, is located along path 40 for focusing the beam. In the preferred embodiment, a movable focusing lens is used. In particular, either a cylinder lens 72 or a spherical lens 74 are movable into or out of the path 40. The cylinder lens 72 is secured in fixed position in a mount 76 secured between a pair of shafts 78 and fittings 80. The cylinder lens 72 can be pivoted into or out of the beam path 40 by means of an external crank 82 extending through one of the fittings 80. Similarly, the spherical lens 74 is secured in fixed position within a mount 86 which is secured between a pair of shafts 88 and fittings 90. The spherical lens 74 can be pivoted into or out of the beam path 40 by means of handle 92. As illustrated, the spherical ends 74 is out of position and the cylinder lens 72 is in position to focus the beam onto mirror 94.

The cylinder lens 72 is utilized when it is desired to focus the beam into a rectangle for performing keratotomies, as shown in FIG. 11. The spherical lens 74 is used when a spot focus is desired, such as for performing a resectomy as shown in FIG. 13.

The mirror 94 can be fixed or movable. In accordance with the preferred embodiment, the mirror 94 is mounted for vertical and pivotal adjustment. In particular, the mirror 94 is pivotally-supported in a mount 96 which in turn is supported on a threaded shaft 98 resting on a bearing 100 inside the housing 68. A pair of guides 102 are also provided for cooperation with opposite sides of the mount 96 to stabilize the mirror 94 and prevent rotation thereof as the shaft 96 is turned in either direction by motor 104 mounted on the housing 68 for vertical adjustment in accordance with the beam focal length desired. A motorized micrometer drive 106 is secured to a lever arm 108 attached to the rear face of mirror 94 for pivotal adjustment in accordance with the position of a mirror 110.

The mirror 94 thus receives the focused beam from lens 72 and reflects it to mirror 110, which can be fixed or movable. In accordance with the preferred embodiment, the mirror 110 is mounted for pivotal adjustment about its own axis and about another offset generally horizontal axis. In particular, mirror 110 is pivotally-supported in a mount 112 which in turn is pivoted between a pair of fittings 114. An external handle 116 extends through one of the fittings 114 in operative association with the mount 112 for pivotal positioning of the mirror 110. Another handle or knob 118 extends through the other fitting 114 in operative association with the mirror 110 for rotational adjustment of the mirror. As illustrated, the second external handle 118 is connected to a small drive pulley 120 which is connected by a belt 122 to a driven pulley 123 connected to the mirror 110 about its axis.

It will thus be appreciated that adjustment of mirrors 94 and 110 permits adjustment as to relocation of the focal plane and lateral positioning of the desired output beam. The shaped and attenuated beam from mirror 38 and the optional insert 64 is focused by either lens 72 or 74 onto mirror 94. The mirror 94 reflects the beam onto mirror 110 which then reflects the beam through a window 124 seated in an opening in the bottom end of the housing 68 and onto the mask 20. The window 124 is preferably formed of sapphire or synthetic quartz so that undue losses do not occur.

Since the output beam passes through window 124 at an angle, a wedge-shaped prism 126 is preferably provided in a bottom end of housing 68 to adjust the direction of the output beam parallel to the rotational axis of the subunit 18 and thus normal to the mask 20.

Referring now to FIGS. 6, 7 and 8, the construction details of the mask 20 can be seen. The mask 20 comprises a circular housing 130 which is adapted for direct attachment to the patient's eye 22 over the cornea. There is no connection between subunit 18 and mask 20, other than optical connection upon predetermined conditions and only for so long as necessary to effect cutting to the desired depth in the cornea, as will be explained more fully below. This also comprises a significant feature of the invention.

The mask 20 can be releasably attached to the patient's eye mechanically or by any other suitable means. As illustrated, a perforated rubber annulus 132 and a conduit 134 connected to a vacuum source (not shown) are provided to form a suction cup by which the mask 20 can be secured in place by vacuum action in protective position over the eye 22.

The mask 20 comprises a partial, generally spherical plate 136 defining a plurality of radial slots 138. The plate 136 is secured within or formed as part of the bottom of housing 130. The slots 138 are circumferentially spaced at uniform intervals and are centered on but radially offset from the axis 140, which is centered on the optical axis of the patient's eye 22. A protective window 142 is mounted in a fitting 144 which in turn is mounted in a central opening in the plate 136 along the axis 140. The window 142 is preferably of material such as glass so that it is opaque to the cutting beam but transparent to visible light. A top plate 146 is rotatably secured to the central fitting 144, and a shutter plate 148 is also rotatably secured to the fitting between the top plate and the fixed bottom plate 136.

The top plate 146 may include one or a pair of symmetrically positioned radial slots. As illustrated, plate 146 includes a single radial slot 150, over which a template 152 is secured. The template 152 defines a single radial cutting control slit 154 of the precise length and width desired, which is smaller than the slot 150 in plate 146 and the cutouts 138 in plate 136. A linear array of sensors 156 are provided in template 152 along opposite sides of the slit 154. As is best seen in FIG. 6, a scale 158 is preferably associated with the plate 146 and housing 130 so that the plate and the template 152 can be positioned over the appropriate cutout 138. A shutter plate 148, however, normally blocks optical communication between plates 136 and 146. If desired, a suitable optical encoder (not shown) can be substituted for the scale 158.

The shutter plate 148 includes a plurality of radial slots 160 equal in number and spacing to the slots 138 in the bottom plate 136. The shutter plate 148 is normally located in closed offset rotational position, by a spring 162 connected between the plate and the housing 130 so that slots 138 and 160 are not aligned. Thus, even when the top plate 146 is positioned with cutting slit 154 in registry with one of the slots 138 in the bottom plate 136, there is no optical communication unless and until the shutter 148 is actuated.

Shutter 148 can be actuated in any suitable manner. As illustrated, a solenoid 164 is connected via cable 166 to the shutter 148. The solenoid 164 is responsive to counter 32 and sensors 156 so that shutter 148 opens only when the beam intensity is even across the cutting slit 154 and is within predetermined limits along the cutting slit, and remains open only for so long as it takes to count down the predetermined number of pulses required to effect cutting to the desired depth.

The system 10 generally operates as follows. Assume that the topology of the patient's cornea has been mapped, that the depth or depths of the incisions desired has been determined, and that the number of pulses required to form incisions of such depth(s) has been determined. The beam from the light source 12 is directed into the base unit 16 along path 34 for reflection and shaping. The mirror 38 in the base unit 16 reflects the beam to the subunit 18, and at the same time shapes the intensity profile of the beam by reason of the absorption film on the mirror. If the light source delivers a circular beam, an insert 64 is provided between the units 16 and 18 so that the configuration of the beam is shaped into a rectangle. The rectangular, attenuated beam is then focused by lens 72 onto mirror 94 which reflects the beam onto mirror 110. The mirror 110 in turn reflects the beam through window 24 and prism 126 out of the subunit 18 and onto the mask 20 covering the patient's eye 22. Mirrors 94 and 110 can be adjusted as necessary to obtain the desired location of the focal plane and lateral positioning of the rectangular beam.

The rectangular beam is applied to a normally closed mask 20 mounted directly on the patient's eye 22. The patient is asked to fixate on a target point to achieve random alignment between mask 20 and subunit 18. The intensity of the beam across and along the control slit 154 on the mask 20 is sensed and compared, and, upon alignment, the shutter plate 148 is opened only when and as long as the measured intensities are within predetermined limits. The control slit 154 of template 152 defines the maximum length and width of each incision. The number of pulses of radiation applied to the eye 22 while the shutter plate 148 is open are counted with counter 32 and compared against the predetermined number of pulses necessary to effect cutting to the desired depth. After the required number of pulses have been applied, the shutter plate 148 is closed to complete one incision, after which the mask 20 can be adjusted for the next incision to be cut. In this manner, precise radial incisions 168 of precise length, width, and depth can be made in the cornea 170 about the optical zone over the iris 172 of a patient's eye 22 during a keratotomy as illustrated in FIG. 11.

To perform a resectomy, as illustrated in FIGS. 12 and 13, the same basic procedure is followed except that the spherical lens 74 is used instead of cylinder lens 72, and the subunit 18 is rotated to form a circular through incision 174 near the outer periphery of the cornea 170. Referring to FIGS. 8 and 9, plates 136, 146 and 148 are removed from mask 20. A rotatable plate 176 is inserted in place of plate 146. As is best seen in FIG. 12, plate 176 includes a central opaque window 178, similar to window 142, and a single radially offset opening 180. As the subunit 18 is rotated, plate 176 is also rotated at the same speed, taking care that cutting hole 180 is always aligned with the light beam. Subunit 18 and plate 176 can be aligned and rotated in unison manually, or mechanically via a suitable interconnecting drive means (not shown).

From this foregoing, it will thus be apparent that the present invention comprises an improved ophthalmic surgery system having numerous advantages over the prior art. One significant advantage involves the use of an ultraviolet/vacuum ultraviolet light source generating a beam of particular characteristics which have been found to be especially well-suited to precision cutting of tissue, particularly corneal tissue. Another significant advantage involves the precision shaping and direction of the beam to a mask mounted directly on the eye of the patient. There is no physical interconnection between the mask and the subunit and alignment is accomplished randomly by fixation on a target point without immobilizing the patient's eye. Sensors on the mask assure optical interconnection only when predetermined conditions are met, and only for so long as necessary to effect cutting to the desired depth. Other advantages will be evident to those skilled in the art.

Although particular embodiments of the invention have been illustrated in the accompanying Drawings and described in the foregoing Detailed Description, it will be understood that the invention is not limited only to the embodiments disclosed, but is intended to embrace any modifications, alternatives, equivalents and-/or substitutions of elements falling within the scope of the invention as defined by the following Claims.

What is claimed is:

1. Apparatus for performing corneal surgery on an eye, comprising:
    means for generating a pulsed light beam in the ultraviolet/vacuum ultraviolet region;
    means for shaping, focusing, and directing the beam toward the eye;
    means for counting the number of pulses of light generated; and
    means covering the eye and responsive to said counting means for selectively exposing predetermined portions of the cornea to the beam for a predetermined number of pulses sufficient to effect cutting of the cornea to the desired depth.

2. The apparatus of claim 1, wherein said light beam generating means produces electromagnetic radiation having a wavelenth between about 1000–2000 angstroms and a power density between about 1 and 10 megawatts per square centimeter.

3. The apparatus of claim 1, wherein said beam generating means comprises a pulsed ArF laser.

4. The apparatus of claim 1, wherein said beam generating means comprises a pulsed KrF laser.

5. The apparatus of claim 1, wherein said beam shaping, focusing, and directing means comprises:
    a base unit connected in optical communication with said beam generating means;
    a subunit having upper and lower ends;
    means for connecting the upper end of said subunit to said base unit in fluid and optical communication and for rotation about a generally upright axis;
    a first mirror mounted in said base unit for reflecting the beam from said beam generating means into the upper end of said subunit, said first mirror being treated to effect predetermined modification of the beam intensity distribution upon reflection;
    a lens mounted in said subunit for focusing the beam from said first mirror;
    a second mirror mounted in said subunit for reflecting the focused beam from said lens;
    a window mounted in the lower end of said subunit offset from the rotational axis of said subunit; and
    a third mirror mounted in said subunit for reflecting the beam from said second mirror through said window out of said subunit.

6. The apparatus according to claim 5, wherein said lens comprises a cylinder lens.

7. The apparatus according to claim 5, wherein said lens comprises a spherical lens.

8. The apparatus according to claim 5, further including:
    means for supporting said second mirror for adjustable linear movement toward and away from said lens, and for adjustable pivotal movement relative to said third mirror; and
    means for supporting said third mirror for adjustable pivotal movement relative to said second mirror and said window.

9. The apparatus according to claim 5, further including:
    a prism mounted in the lower end of said subunit adjacent to said window for effecting projection of the beam passing through said window in a direction substantially parallel to but offset from the rotational axis of said subunit.

10. The apparatus of claim 1, wherein said counting means comprises:
    a beam splitter; and a photo diode counter coupled to said beam splitter for sensing pulses of light.

11. The apparatus of claim 1, wherein said eye covering means comprises:
an opaque mask including an offset predetermined control slit defining the shape of the incision to be cut into the cornea;
means for releasably securing said mask to the eye over the cornea;
a central window in said mask formed of material opaque to the cutting light beam but transparent to visible light;
an array of sensors positioned along opposite sides of the control slit in said mask;
a shutter mounted on said mask for movement into and out of blocking position relative to the control slit;
means for normally biasing said shutter to a blocking position; and
means responsive to said sensors and said counting means for opening said shutter to expose the cornea to the beam only when the measured beam intensities on opposite sides of the control slit are within predetermined limits and only for a predetermined number of pulses.

12. Apparatus for performing corneal surgery on an eye, comprising:
means for generating a pulsed light beam in the ultraviolet/vacuum ultraviolet region having a wavelength of about 1000–2000 Angstroms and a power density of about 1–10 megawatts per square centimeter;
a base unit connected in optical communication with said beam generating means;
means for counting the number of pulses of light generated and delivered to said base unit;
a subunit having upper and lower ends;
means for connecting the upper end of said subunit to said base unit in fluid and optical communication and for rotation about a generally upright axis;
a first mirror mounted in said base unit for shaping the normal intensity distribution of the beam from said beam generating means and reflecting the shaped beam into the upper end of said subunit;
a lens mounted in said subunit for focusing the beam from said first mirror;
a second mirror mounted in said subunit for reflecting the focused beam from said lens;
a window mounted in the lower end of said subunit;
a third mirror mounted in said subunit for reflecting the beam from said second mirror through said window out of said subunit; and
means covering the eye and responsive to said counting means for selectively exposing predetermined portions of the cornea to the beam for a predetermined number of pulses sufficient to effect cutting of the cornea to the desired depth.

13. The apparatus according to claim 12, wherein said lens comprises a cylinder lens.

14. The apparatus according to claim 12, wherein said lens comprises a spherical lens.

15. The apparatus according to claim 12, further including:
means for supporting said second mirror for adjustable linear movement toward and away from said lens, and for adjustable pivotal movement relative to said third mirror; and
means for supporting said third mirror for adjustable pivotal movement relative to said second mirror and said window.

16. The apparatus according to claim 12, further including:
a prism mounted in the lower end of said subunit adjacent to said window for effecting projection of the beam passing through said window in a direction substantially parallel to but offset from the rotational axis of said subunit.

17. The apparatus of claim 12, wherein said counting means comprises:
a beam splitter; and
a photo diode counter coupled to said beam splitter for sensing pulses of light.

18. The apparatus of claim 12, wherein said eye covering means comprises:
an opaque mask including an offset predetermined control slit defining the shape of the incision to be cut into the cornea;
means for releasably securing said mask to the eye over the cornea;
a central window in said mask formed of material opaque to the beam but transparent to visible light;
an array of sensors positioned along opposite sides of the control slit in said mask;
a shutter mounted on said mask for movement into and out of blocking position relative to the control slit;
means for normally biasing said shutter to a blocking position; and
means responsive to said sensors and said counting means for opening said shutter to expose the cornea to the beam only when the measured beam intensities on opposite sides of the control slit are within predetermined limits and only for a predetermined number of pulses.

19. A method for performing corneal surgery on an eye, comprising the steps of:
(a) providing a light source;
(b) generating with the light source a pulsed light cutting beam in the ultraviolet/vacuum ultraviolet region;
(c) positioning between the eye and light source a shutter with a normally closed control slit offset from the optical axis of the eye;
(d) modifying the normal intensity distribution of the cutting beam;
(e) focusing the modified beam;
(f) projecting the modified, focused beam on the shutter;
(g) sensing the beam intensity across the control slit of the shutter;
(h) opening the shutter to expose the cornea to the modified, focused beam when the measured beam intensities across the control slit are within predetermined limits;
(i) counting the beam pulses applied to the cornea while the shutter is open; and
(j) closing the shutter after a predetermined number of pulses have been applied to form a corneal incision of predetermined shape, length, width and depth.

20. The method of claim 19, wherein the light beam has a wavelength between about 1000 and 2000 angstroms and a power density between about 1 and 10 megawatts per square centimeter.

21. The method of claim 19, further including the step of:
rotating the shutter relative to the eye so that successive circumferentially spaced-apart radial incisions about a central uncut portion of the cornea can be formed.

22. The method according to claim 21, wherein step (e) is accomplished with a cylinder lens.

23. The method of claim 19, further including the step of: rotating the shutter relative to the eye so that a circular incision can be formed about a central uncut portion of the cornea.

24. The method according to claim 23, wherein step (e) is accomplished with a spherical lens.

25. The method of claim 19, wherein step (d) is accomplished by reflection with a mirror covered with a partiallyabsorbing film of variable density.

26. The method of claim 19, wherein the shutter is attached directly to the eye over the cornea.

27. The method of claim 19, further including the step of: positioning along the optical axis between the eye and the light source a window of material that is opaque to the cutting beam but transparent to visible light.

* * * * *